United States Patent [19]
Conway

[11] Patent Number: 5,778,457
[45] Date of Patent: Jul. 14, 1998

[54] HYGIENIC PANTY AND QUICK-ATTACH PAD

[75] Inventor: David W. Conway, Loveland, Ohio

[73] Assignee: Intellitecs International Ltd., Cincinnati, Ohio

[21] Appl. No.: 597,132

[22] Filed: Feb. 6, 1996

Related U.S. Application Data

[63] Continuation-in-part of Ser. No. 575,623, Dec. 20, 1995.

[51] Int. Cl.⁶ .................... A41B 9/00; A41B 9/12
[52] U.S. Cl. .................... 2/406; 2/400; 2/267; 604/385.1
[58] Field of Search ................. 2/400, 401, 402, 2/403, 404, 405, 406, 407, 408, 48, 46, 49.1, 49.2, 49.3, 49.4, 49.5, 50, 51, 52, 111, 112, 69, 69.5; 604/385.1, 396, 386

[56] References Cited

U.S. PATENT DOCUMENTS

| H1298 | 4/1994 | Ahr et al. | |
| Re. 30,972 | 6/1982 | Kyle et al. | |
| 3,308,826 | 3/1967 | Blake . | |
| 3,368,563 | 2/1968 | Scheier | 604/396 |
| 3,481,337 | 12/1969 | Ruffo . | |
| 3,699,966 | 10/1972 | Chapuis . | |
| 3,709,221 | 1/1973 | Riely . | |
| 3,717,150 | 2/1973 | Schwartz . | |
| 3,749,095 | 7/1973 | Toyama | 604/396 |
| 3,888,256 | 6/1975 | Studinger . | |
| 3,901,240 | 8/1975 | Hoey . | |
| 3,955,575 | 5/1976 | Okuda . | |
| 3,971,381 | 7/1976 | Gibson . | |
| 4,021,870 | 5/1977 | Walters . | |
| 4,128,686 | 12/1978 | Kyle et al. | |
| 4,244,367 | 1/1981 | Rollenhagen . | |
| 4,352,356 | 10/1982 | Tong . | |
| 4,572,174 | 2/1986 | Eilender et al. | |
| 4,627,122 | 12/1986 | Hopp . | |
| 4,704,745 | 11/1987 | Reaver | 2/268 |
| 4,850,987 | 7/1989 | Gilomen . | |
| 4,981,480 | 1/1991 | Gaudet et al. | |
| 5,032,122 | 7/1991 | Noel et al. | 604/386 |
| 5,065,600 | 11/1991 | Byles . | |
| 5,210,882 | 5/1993 | Moretz et al. | |
| 5,217,782 | 6/1993 | Moretz et al. | |
| 5,236,428 | 8/1993 | Zajaczkowski | 604/385.1 |

(List continued on next page.)

FOREIGN PATENT DOCUMENTS

| 509028 | 2/1977 | Australia . |
| 1192701 | 9/1985 | Canada . |
| 1810867 | 11/1968 | Germany . |
| 8503430 | 8/1985 | WIPO . |
| WO8605386 | 9/1986 | WIPO . |
| 9008524 | 8/1990 | WIPO . |

OTHER PUBLICATIONS

International Search Report mailed May 22, 1997; 3 pages (International Application No. PCT/US 96/19844).

*Primary Examiner*—Jeanette E. Chapman
*Attorney, Agent, or Firm*—Wood, Herron & Evans, L.L.P.

[57] ABSTRACT

A quick-attach absorbent pad 14 for use with a panty 10 is provided with an upper surface 16 and a lower surface 18, the pad 14 being sized to fit against a crotch panel 12 of a panty 10 with the lower surface 18 of the pad 14 adjacent the crotch panel 12. The pad 14 further includes a plurality of hook fasteners 20 associated with the pad lower surface 18, which enables the pad 14 to be readily attached to the undergarment 10, and which prevents the pad 14 from shifting during use. Also provided is a panty 10 having a thin yet absorbent crotch panel 12. In a preferred embodiment of the panty 10, the crotch panel 12 includes a fluid absorbent layer 38 overlying a fluid barrier 40. The fluid absorbent layer 38 preferably is made of a single-ply fabric having a hydrophobic upper surface 42 facing toward the user and a hydrophilic lower surface 44 facing away from the user. In addition, the upper surface 42 preferably includes yarn loops 90 which releasably hold to the hook fasteners 20 on the absorbent pad 14, thereby maintaining the pad 14 in position on the undergarment 10.

40 Claims, 3 Drawing Sheets

U.S. PATENT DOCUMENTS

| | | |
|---|---|---|
| 5,249,320 | 10/1993 | Moretz et al. . |
| 5,261,901 | 11/1993 | Guay . |
| 5,269,720 | 12/1993 | Moretz et al. . |
| 5,290,269 | 3/1994 | Heiman . |
| 5,291,617 | 3/1994 | Moretz et al. . |
| 5,296,290 | 3/1994 | Brassington . |
| 5,297,296 | 3/1994 | Moretz et al. . |
| 5,300,058 | 4/1994 | Goulait et al. . |
| 5,306,536 | 4/1994 | Moretz et al. . |
| 5,315,717 | 5/1994 | Moretz et al. . |
| 5,392,467 | 2/1995 | Moretz et al. . |
| 5,414,870 | 5/1995 | Moretz et al. . |
| 5,415,650 | 5/1995 | Sigl .................................... 604/387 |
| 5,435,014 | 7/1995 | Moretz et al. . |
| 5,507,735 | 4/1996 | Van Iten et al. ........................ 604/386 |

HYGIENIC PANTY AND QUICK-ATTACH PAD

CROSS-REFERENCE TO RELATED APPLICATION

This application is a continuation-in-part of my U.S. patent application Ser. No. 08/575,623, entitled "INFANT T-SHIRT" and filed on Dec. 20, 1995, the disclosure of which is incorporated herein in its entirety by reference.

BACKGROUND OF THE INVENTION

1. Field of the Invention

The present invention relates to undergarments such as a woman's panty and, more particularly, to such undergarments having an absorbent panel and to absorbent pad inserts for such undergarments.

2. Description of Prior Art

Undergarments having an absorbent panel are often used to assist in managing bodily discharge, such as incontinent or menstrual discharge. Such undergarments may be in the form of a woman's panty having a body portion, a waist opening, a pair of leg openings and a crotch area between the leg openings. Such undergarments generally include an absorbent panel permanently positioned, along with the fabric crotch panel of the panty, in the crotch area which is designed to absorb fluid from such discharges. The absorbent panel typically includes several layers of different materials having varying thicknesses, in order to provide the necessary absorbing and retaining effect. However, such absorbent panels tend to be extremely thick and bulky, and therefore, are quite uncomfortable for the user.

To eliminate the bulk and discomfort, some women prefer to use panties without a permanent crotch panel abutting the crotch area, in combination with disposable absorbent insert pads (i.e. sanitary pads) that may be temporarily placed in a conventional panty and then removed and disposed of after use. Such pads are sized to fit in the crotch area of the undergarment, and typically include one or more absorbent layers and adhesive strip or strips to temporarily hold the pad in the panty. The pad also has a paper backing to cover and protect the adhesive strips during storage and to prevent multiple pads from sticking to each other in the package. With these pads, a woman must remove and dispose of the paper backing, and orient and manipulate the pad onto the crotch area of the panty, all without having the adhesive contact and stick to some other garment or part of the panty. In addition, such pads have a limited fluid capacity, and once this capacity has been met, any excess discharge simply leaks over the pad edges and seeps into the undergarment itself, thereby soiling the undergarment and possibly the outer clothing as well. Yet increasing the dimensions of these pads is not a particularly desirable option because the increased size would make the pads bulky and uncomfortable. Furthermore, such pads may shift in use because the pad adhesive tends to become less effective when wet.

SUMMARY OF THE INVENTION

The present invention overcomes the above-mentioned drawbacks by providing a quick-attach absorbent pad designed to be easily positioned on and removed from the crotch area of an undergarment. The pad also is designed so as to maintain its position on the undergarment without shifting, even when wet. To this end and in accordance with one aspect of the present invention, instead of adhesive strips and backing paper, the quick-attach absorbent pad includes a plurality of hook fasteners associated with the pad lower surface. The hook fasteners enable the pad to be readily attached to yarn loops in the crotch area of the undergarment, and prevent the pad from shifting during use. The hooks do not require use of backing paper cover strips and do not rely on adhesive to attach to the panty thereby overcoming problems previously encountered with such products.

In a preferred embodiment, the absorbent pad upper surface is essentially devoid of yarn loops. This absence of yarn loops enables multiple pads to be stacked together, such as for product packaging, without the hook fasteners from one pad fastening to the upper surface of an adjacent pad. Consequently, no cover strips are necessary. The hook fasteners are attached to a hook fastener base which is sized so as to be attached to only an insubstantial portion of the pad lower surface, thereby minimizing obstruction of air communication with the lower surface. In addition, the fastener base preferably includes one or more apertures, thereby increasing the amount of air communication with the pad lower surface and increasing flexibility of the pad. Preferably, the pad is made up of materials which are disposable so that the pad may be thrown away after use.

The present invention also provides a panty having an absorbent crotch panel designed to be thin and flexible, yet able to absorb and retain overrun of urine or other fluids, so as to maintain user comfort and confidence, and inhibit soiling of outer clothing.

In a preferred embodiment, the crotch panel includes a fluid absorbent layer designed to absorb fluid (such as excess fluid not retained by the removable pad), as well as a fluid barrier layer to prevent fluid from passing through the crotch panel and into the outer clothing. The fluid absorbent layer preferably is made of an advantageously thin, single-ply fabric having an upper surface facing toward the user and a lower surface facing away from the user. The upper surface includes yarn loops which releasably hold to the hook fasteners associated with the absorbent pad, thereby maintaining the pad in position on the undergarment. In addition, the upper surface has hydrophobic properties while the lower surface has hydrophilic properties. With such a fabric, the excess fluid not absorbed by the absorbent pad is wicked from the inner surface of the crotch panel toward the lower or hydrophilic surface of the absorbent layer, where the excess fluid is retained. In this regard, the surface of the crotch panel adjacent the user has a "dry feel". Moreover, the barrier layer prevents fluid from leaking through the crotch panel and onto outer clothing. Preferably, the barrier layer has very thin first and second plies, with the first ply being a fluid barrier material and the second ply being a fabric ply. If desired, this outer fabric second ply may define the outer surface of the panty in the crotch area. Alternatively, the outer surface of the crotch area of the panty may be a continuation of the material used to form the remainder of the panty. Preferably, the panty and crotch panel are made of washable materials, thereby enabling the panty to be washed and used numerous times.

By virtue of the foregoing, there is thereby provided a quick-attach absorbent pad for absorbing fluid discharge, which is easy to make and does not suffer from the drawbacks of adhesive strip fasteners. There is thus further provided a panty having a fluid absorbing and retaining crotch panel which is thin and comfortable yet holds excess fluids (such as those not absorbed by the removable pad), thereby enhancing user comfort and confidence and preventing soiling of outer clothing. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to explain the principles of the invention.

DETAILED DESCRIPTION OF THE DRAWINGS

Figure 1:
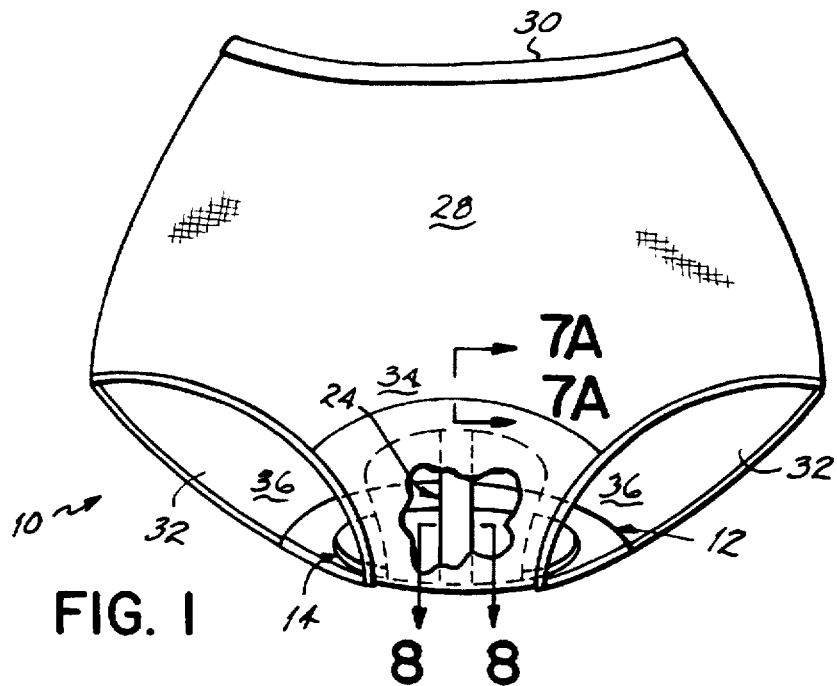
FIG. 1 is a front, partially broken away view of a woman's panty with a quick-attach absorbent pad attached to the crotch panel thereof in accordance with the principles of the present invention.
Figure 2:
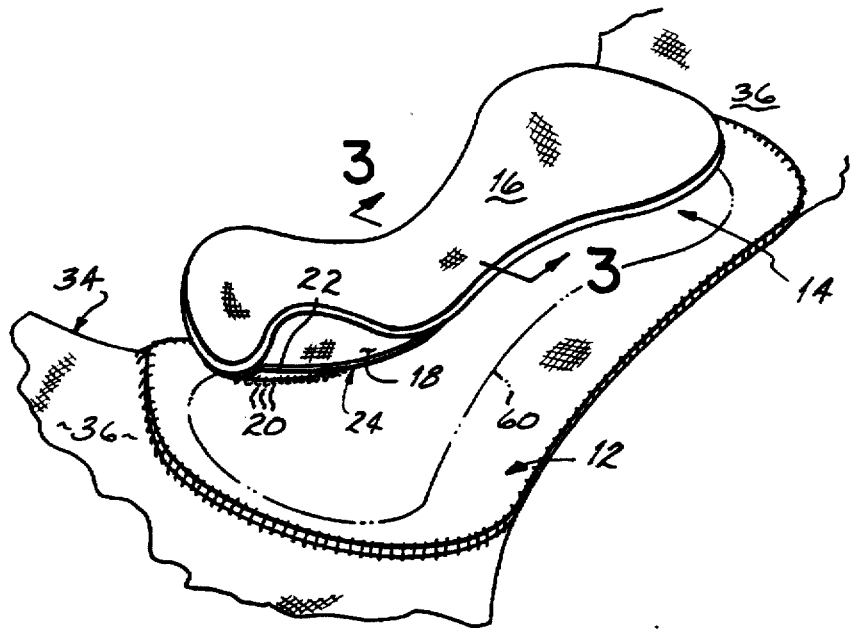
FIG. 2 is a perspective view of the crotch area of the woman's panty of FIG. 1, with the quick-attach absorbent pad elevated above the undergarment.
Figure 3:
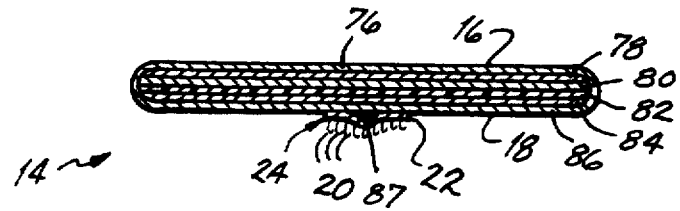
FIG. 3 is a schematic cross-sectional view of the quick-attach absorbent pad of FIG. 2 taken along line 3—3.
Figure 4A:
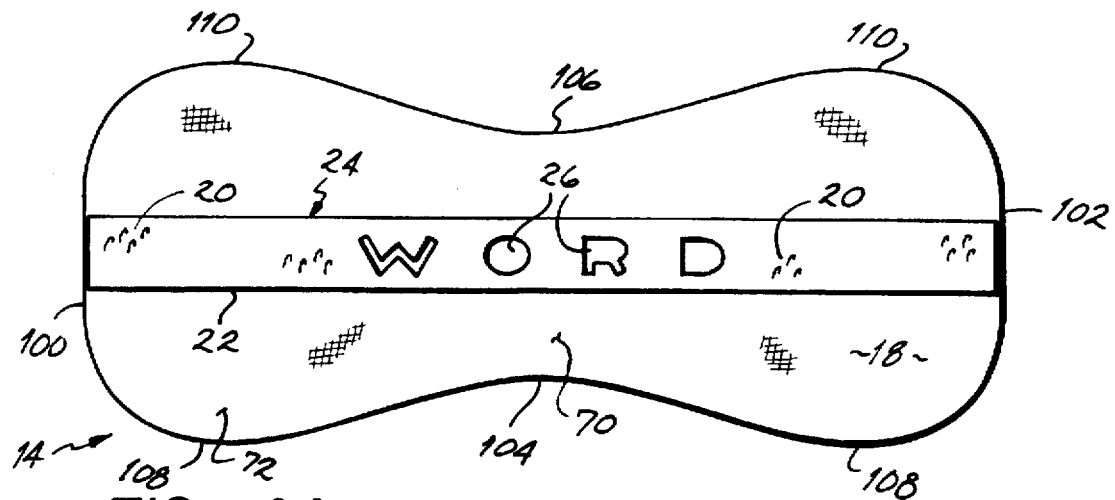
FIG. 4A is a bottom view of an embodiment of the quick-attach absorbent pad.
Figure 4B:
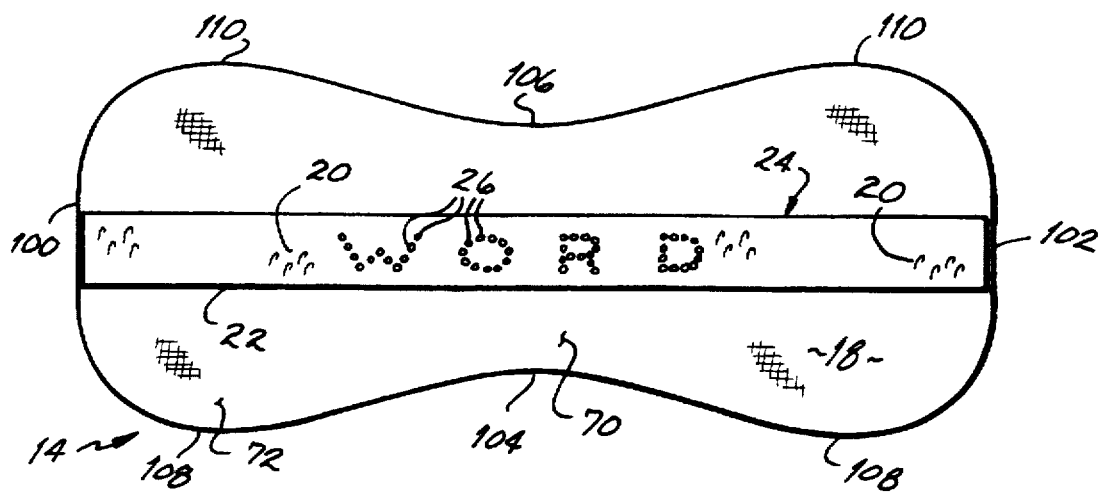
FIG. 4B is a bottom view similar to FIG. 4A but showing an alternative embodiment of the quick-attach absorbent pad.

With reference to FIG. 1, there is shown a panty 10 having an absorbent crotch panel 12 and a quick-attach absorbent pad 14 releasably attached to the crotch panel 12, both of which incorporate the features of the present invention. With reference to FIGS. 2–4, the quick-attach absorbent pad 14 includes an upper surface 16 and a lower surface 18, and is sized to fit against the crotch panel 12 of a panty 10 with the lower surface 18 of the pad 14 adjacent the crotch panel 12. As best shown in FIGS. 3 and 4, the pad 14 further includes a plurality of hook fasteners 20 associated with the pad lower surface 18. To this end, hooks 20 extend from and are supported by a hook fastener base 22 attached, such as with adhesive, to the pad lower surface 18. With reference to FIGS. 4A and 4B, the hook fastener base 22 is provided in the form of a strip 24 (or a plurality of such strips) oriented along the lower surface 18 of the pad 14. The strip 24 is sized so as to cover only an insubstantial portion of the pad lower surface 18, thereby minimizing obstruction of air flow to the pad lower surface 18. Furthermore, the base 22 includes one or more apertures or holes 26 which further assist in allowing air to communicate with the pad lower surface 18 and increase flexibility of the pad 14. If desired, these apertures 26 may be oriented so as to form a particular pattern in the hook fastener base 22. For example, in the embodiment shown in FIG. 4A, the apertures 26 are in the form of letter cutouts, as exemplified by "word". In an alternate embodiment shown in FIG. 4B, the apertures 26 are in the form of a plurality of round openings, positioned on the hook fastener base 22 in such a way as to define a pattern, also exemplified by "word". With respect to pad size, and with reference to FIGS. 4A and 4B, an exemplary pad 14 may have a generally hour-glass shape, with a length of about 8 in. extending between left and right edges 100, 102, a width of about 2.5 in. between inner lateral edges 104, 106 in the narrow waist region 70 extending outward to a width of about 3.5 in. between outer lateral edges 108, 110 in the broader shoulder regions 72 of the pad, and a thickness between upper and lower surface 16, 18 of about 0.5 in. In addition, the hook fastener base 22 may be in the form of a strip 24, as shown in FIGS. 4A and 4B, with the strip 24 having a length of about 8 in., a width of about 1 in., and a thickness of about $1/32$ in. including the hooks fasteners, such that the strip 24 covers an insubstantial portion of the pad lower surface 18.

The quick-attach absorbent pad 14 may be formed either of disposable or washable, reusable materials, with disposable materials being preferred. For example, with reference to FIG. 3, the pad 14 may include, from top to bottom, an upper nonwoven layer 76, an intermediate wood pulp layer 78, a superabsorbent core 80, another intermediate wood pulp layer 84 and a lower nonwoven layer 86. In addition, the pad 14 may include a liquid barrier layer, such as a liquid impermeable polyliner 82 disposed between the superabsorbent core 80 and intermediate wood pulp layer 84, so as to inhibit the fluid from moving through the pad 14 into the panty 10. Layer 82 could be a breathable membrane to provide a fluid barrier, but which allows moisture vapor to pass therethrough. The upper nonwoven layer 76 and lower nonwoven layer 86 may be formed of a single, tubular sheet joined by adhesive, as at 87, or may be formed of a pair of sheets adhered together along the pad edges. The hook fastener base strip 24 with a plurality of hook fasteners 20 extending therefrom is attached to the lower nonwoven layer 86 such as along glue line 87. Strip 24 may be attached with additional adhesive (not shown) and/or adhesive 87. The hook fasteners 20 may be Velcro®-type hook fasteners extending from a hook fastener base 22, to provide J-shaped hook members 112 (FIG. 7A) or mushroom-shaped hook members 114 (FIG. 7B), the latter being available as part No. XMH4152 from 3M. The apertures 26 may be provided in the base 22 using a die cutting process or the like.

Figure 5:
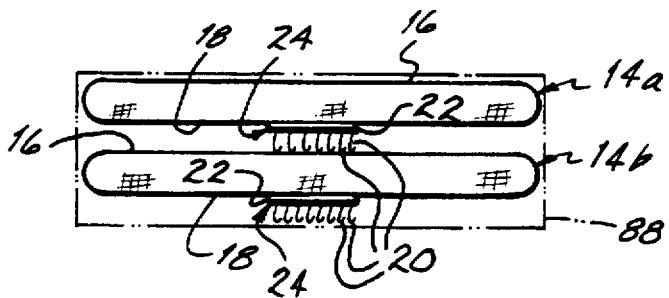
FIG. 5 is a schematic cross-sectional view of a pair of quick-attach absorbent pads of FIG. 1 stacked in a product package.

The pad upper surface 16 preferably is essentially devoid of yarn loops so that multiple pads 14 may be stacked on top of one another, without the hook fasteners 20 on the lower surface 18 of one pad 14 holding onto the upper surface 16 of an adjacent pad 14. In this manner, and with reference to FIG. 5, several quick-attach absorbent pads 14 may be placed together in a single product package 88 without attaching to one another. As seen in FIG. 5, a first pad 14a is stacked on top of a second pad 14b, with the hook fasteners 20 of the first pad 14a pressed against the upper surface 16 of the second pad 14b. Yet, because the pad upper surface 16 is essentially devoid of yarn loops, the pads 14a, 14b are not fastened together. Alternatively, each pad 14 may be in a further self-contained wrapper (not shown). In that case, hook fasteners 20 will not attach to the wrapper.

Figure 6A:
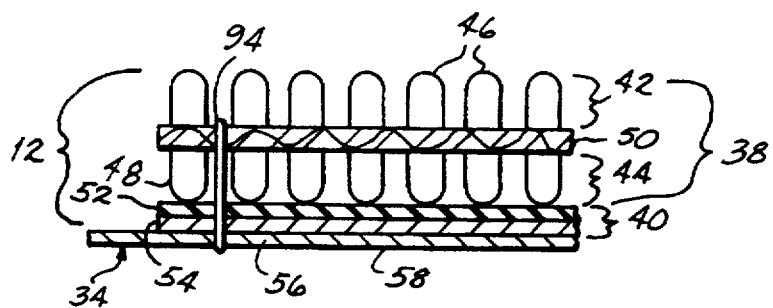
FIG. 6A is a schematic cross-sectional view of a portion of the panty and crotch panel taken along line 6A—6A of FIG. 1.
Figure 6B:
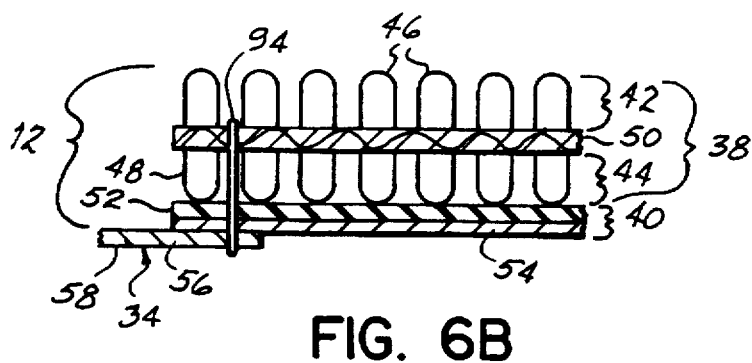
FIG. 6B is a schematic cross-sectional view similar to FIG. 6A but showing an alternative embodiment of the panty.
Figure 7A:
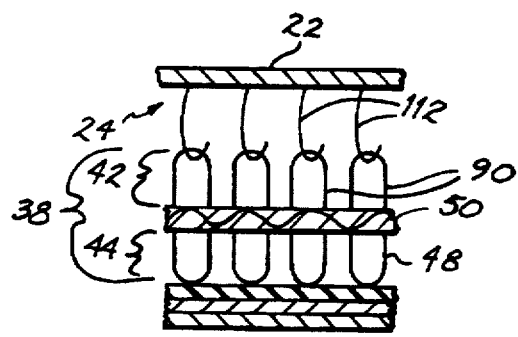
FIG. 7A is a schematic cross-sectional view of a portion of the quick-attach absorbent pad, crotch panel and panty of FIG. 1 taken along line 7A—7A.
Figure 7B:
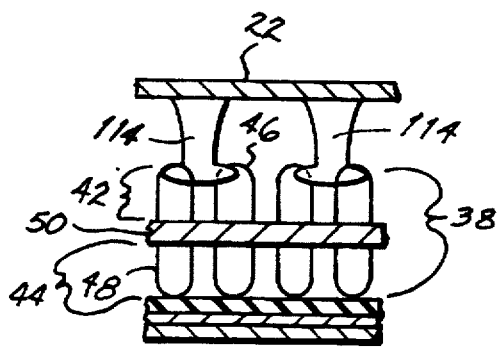
FIG. 7B is a view similar to FIG. 7A but showing an alternative hook fastener.

With further reference to FIG. 1, the panty 10 of the present invention includes a body portion 28, an upper waist opening 30, a pair of lower leg openings 32 and a crotch area 34 disposed between the leg openings 32. The crotch area 34 includes a crotch panel 12 overlying the inner surface 36 of the crotch area 34 and peripherally stitched to the panty 10. With reference to FIGS. 6A and 6B, the crotch panel 12 includes a thin body-facing absorbent layer 38 overlying a thin panty-facing barrier layer 40. The absorbent layer 38 is a single-ply fabric, fluid-absorbent layer having an upper surface 42 and a lower surface 44, with the upper surface having hydrophobic properties and the lower surface having hydrophilic properties, whereby any fluid at the upper surface 42 is wicked through the upper hydrophobic surface 42 and toward the lower hydrophilic surface 44, where it is retained away from the user's body. The absorbent layer 38 preferably has polyester or polypropylene yarns 46 defining the upper hydrophobic surface 42, cotton yarns 48 defining the lower hydrophilic surface 44 and a ground yarn or yarns 50, in the manner shown and described in FIGS. 3 and 8, and the accompanying text, of U.S. Pat. No. 5,290,296, the entire disclosure of which is incorporated herein by reference. With reference to FIGS. 7A and 7B hereof, it is important to note that the yarns 46 defining the upper surface 42 of the absorbent layer 38 are joined to the other yarns so as to define a plurality of loops 90 to be held by the J-shaped hook members 112 or mushroom-shaped hook members 114, respectively, of the hook fasteners 20 of the quick-attach absorbent pad 14.

The barrier layer 40 is provided to prevent excess fluid retained in the absorbent layer 38 from passing through the crotch panel 12 and out onto further clothing layers. As shown in FIG. 6A, the barrier layer 40 includes a first ply 52 and a second ply 54. The first ply 52 is a fluid barrier material such as a thin layer of polyurethane film, while the second ply 54 is a fabric ply such as a polyester tricot knit, with the polyurethane being laminated or coated to the knit fabric. The absorbent layer 38 and the barrier layer 40 are joined to each other by the same peripheral stitching 94 used to attach the crotch panel 12 to the panty 10.

In the panty embodiment shown in FIG. 6A, the fabric 56 used to form the body portion 28 of the panty 10 extends all the way through the crotch area 34 of the undergarment. Therefore, the outer surface 58 of the crotch area 34 of the panty 10 is formed of this material 56. The crotch panel 12 is positioned in an overlying position on the body facing side of this material 56 with the barrier second ply 54 facing thereupon, and is peripherally stitched (as at 94) to the fabric 56 used to form the body portion 28, as is shown in FIG. 2. The peripheral stitching thread may be made of any suitable material, and preferably is a polyester/cotton blend thread, thereby assisting in the wicking action.

In the alternative panty embodiment shown in FIG. 6B, the material 56 used to form the body portion 28 of the panty 10 generally does not extend down through the crotch area 34 of the panty 10. Instead, the outer surface 58 of the crotch area 34 of the panty 12 is defined by the second ply 54 of the barrier layer 40. The material 56 used to form the remainder of the body portion 28 of the panty 10 slightly overlaps the crotch panel 12 so that the crotch panel 12 may be peripherally stitched (as at 94) to this material 56 using a polyester/cotton blend thread or the like.

Figure 6C:
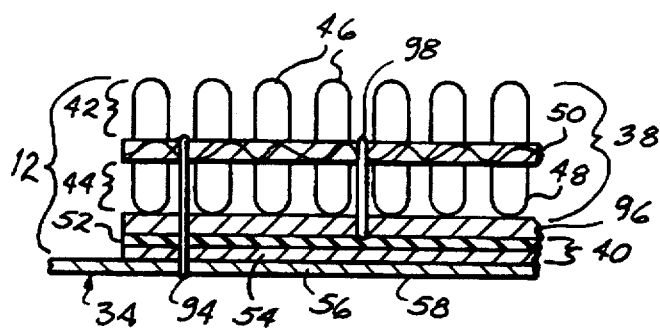
FIG. 6C is a schematic cross-sectional view similar to FIG. 6A but showing yet another alternative embodiment of the panty.

With reference to FIG. 6C, yet another panty embodiment includes an additional fabric layer 96, for example a felted nonwoven fabric, positioned between the absorbent layer 38 and the barrier layer 40 of the crotch panel 12. The additional fabric layer 96 is attached to the absorbent layer 38 by quilting (as at 98), and these two layers 38, 96 are peripherally stitched 94 to the barrier layer 40 and outer panty fabric 56. Such an additional fabric layer 96 may be a felt layer quilted to the absorbent layer 38 as shown and described in FIGS. 6, 7 and 9, and the accompanying text of U.S. Pat. No. 5,290,296.

With reference to FIG. 2, the upper surface of the crotch panel 12 may include a target marking 60 which corresponds approximately to the peripheral shape of the pad 14, by which to indicate a target for the proper positioning of the quick-attach absorbent pad 14 on the panel 12. The target marking 60 may be printed onto absorbent layer 38 or stitched therethrough. The materials used to form the panty 10 and crotch panel 12 preferably are washable so that the panty 10 may be washed and reused several times.

In use, the user (not shown) may simply lift a first quick-attach absorbent pad 14a from a package 88 of multiple pads (see FIG. 5), and quickly position the pad 14a in a secure and releasable position on the crotch panel 12, simply by urging the lower surface 18 of the pad 14a toward the upper surface 42 of the crotch panel 12 absorbent layer 38 so that the hook fasteners 20 of the pad 14 may engage the yarn loops 90 on the upper surface 42. With the pad 14 positioned in place, the user may wear the panty 10 just like any other traditional panty. Because both the detachable absorbent pad 14 and the crotch panel 12 are relatively thin and flexible, the pad 14 and panty 10 combination is comfortable for the user. In addition, because the combination is thin and nonbulky, the panty 10 provides an outward appearance of being a conventional undergarment.

In most instances, the absorbent pad 14 is able to absorb virtually all the fluid from a single discharge; and in some cases, the pad 14 is able to absorb fluid from a subsequent discharge or discharges, depending upon the volume of fluid. However, any excess fluid not absorbed by the pad 14 is absorbed by the absorbent layer 38 of the crotch panel 12 and retained in the crotch panel 12 by the barrier layer 40, thereby preventing seepage or strike-through of fluid to the outer clothing. In the case of a light or moderate discharge captured entirely by the absorbent pad 14, the user may simply remove and dispose of the pad 14, and position a new one (e.g. pad 14b) on the crotch area 34 of the panty 10. Alternatively, or after a heavier discharge, the user may remove and dispose of the pad 14, and wash the panty 10 in a conventional washer and dryer before applying a new pad 14b. In some instances, the woman may not need the absorbency of the pad 14 and so may wear just the panty 10, thereby relying on the crotch panel 12 for its absorbing characteristics.

By virtue of the foregoing, there is thus provided a quick-attach absorbent pad 14 and a panty 10 with an improved crotch panel 12 which assists in managing discharged fluids, while enhancing patient comfort and preventing outer clothing from becoming soiled.

While the present invention has been illustrated by description of embodiments, and while the illustrative embodiments have been described in considerable detail, it is not the intention of the inventor to restrict or in any way limit the scope of the appended claims to such detail. Additional advantages and modifications will readily appear to those skilled in the art. By way of example, the hook fasteners 20 may be distributed across substantially all of the pad lower surface 18. Also, the crotch panel 12 may extend upward toward the waist in the front and/or over the buttocks in the back of the undergarment 10, or may merely be a fabric layer having loop yarns for attachment with pads 14. Further, panel 12 may be associated with the crotch area 34 by being attached to panty 10 only at its distal ends, so as to float like a sling in the panty 10. Additionally, the undergarment 10 may be in the form of a man's brief. The invention in its broader aspects is therefore not limited to the specific details, representative apparatus and methods, and illustrative examples shown and described. Accordingly, departures may be made from such details without departing from the spirit or scope of Applicant's general inventive concept.

Having described the invention, what is claimed is:

1. A quick-attach absorbent pad for use with an undergarment, the pad comprising:
   an upper surface and a lower surface containing a fluid absorbent material therebetween and being sized to fit against a crotch panel of said undergarment with the lower surface of the pad adjacent said crotch panel, the pad further comprising a plurality of hook fasteners associated with the pad lower surface and adapted to releasably attach the pad to yarn loops of said crotch panel, the pad further comprising a hook fastener base attached to the pad lower surface and supporting the plurality of hook fasteners, wherein the base includes at least one aperture through which air may communicate with the pad lower surface.

2. The pad of claim 1, the pad upper surface being essentially devoid of yarn loops wherein a first said pad may be stacked, lower surface down, on top of a second said pad, upper surface up, without either of said pads holding to one another.

3. The pad of claim 1 wherein the base includes a plurality of the apertures.

4. The pad of claim 3 wherein the apertures are oriented so as to form a pattern in the base.

5. The pad of claim 1, the base being attached to only an insubstantial portion of the pad lower surface thereby minimizing obstruction of air communication with the lower surface.

6. The pad of claim 1 being comprised of disposable materials whereby the pad may be disposed of after use.

7. The pad of claim 1 wherein the pad includes a liquid barrier layer.

8. The pad of claim 1 in combination with an undergarment having a crotch panel, the crotch panel including yarn loops for being releasably held by the hook fasteners of the pad.

9. The combination of claim 8, the undergarment and crotch panel being comprised of washable materials whereby the undergarment is reusable.

10. The combination of claim 9, the pad being comprised of disposable materials whereby the pad may be disposed of after use.

11. The combination of claim 8 wherein the crotch panel includes an absorbent layer whereby fluid not retained by the pad may be absorbed by the absorbent layer.

12. The combination of claim 1 wherein the absorbent layer includes upper and lower surfaces, the upper surface having hydrophobic properties and the lower surface having hydrophilic properties, whereby fluid at the upper surface tends to wick towards the lower surface.

13. The combination of claim 11 wherein the crotch panel further includes a barrier layer underlying the absorbent layer, the barrier layer inhibiting fluid from passing through the crotch panel.

14. The pad of claim 1 wherein the plurality of hook fasteners are oriented in a substantially parallel pattern relative to the longitudinal axis of the pad.

15. The pad of claim 14 wherein the plurality of hook fasteners are oriented so as to substantially form a strip or band of hook fasteners.

16. The pad of claim 14 wherein the plurality of hook fasteners are oriented so as to substantially form a plurality of strips or bands of hook fasteners.

17. The pad of claim 1 wherein the hook fastener base is oriented substantially parallel to the longitudinal axis of the pad.

18. The pad of claim 17 wherein the hook fastener base extends between the ends of the pad and along the interior region of the pad lower surface.

19. The pad of claim 1 wherein the plurality of hook fasteners is selected from the group consisting of J-shaped hook fasteners, mushroom-shaped hooked fasteners, and combinations thereof.

20. The pad of claim 1 wherein the lower surface is liquid permeable.

21. The combination of claim 20 wherein the crotch panel includes an additional fabric layer disposed between the absorbent layer and the barrier layer.

22. The combination of claim 21 wherein the additional fabric layer and the absorbent layer are quilted together.

23. The combination of claim 21 wherein the crotch panel includes a target marking which indicates the proper placement of the pad on the crotch panel.

24. The combination of claim 21 wherein the undergarment is a panty.

25. In combination:
   a quick-attach absorbent pad for use with an undergarment, the pad comprising an upper surface and a lower surface containing a fluid absorbent material therebetween and being sized to fit against a crotch panel of said undergarment with the lower surface of the pad adjacent said crotch panel, the pad further comprising a plurality of hook fasteners associated with the pad lower surface and adapted to releasably attach the pad to yarn loops of said crotch panel, and
   an undergarment having a crotch panel, the crotch panel including yarn loops for being releasably held by the hook fasteners of the pad wherein the crotch panel includes a target marking which indicates the proper placement of the pad on the crotch panel.

26. An undergarment for use with an absorbent pad, the undergarment comprising:
   a body portion with an upper waist opening and two lower leg openings defining a crotch area therebetween, the body portion having a crotch panel associated with the crotch area, the crotch panel including a single-ply fluid absorbent fabric layer having upper and lower surfaces, the upper surface including loop yarns for being releasably held by said pad, the upper surface further having hydrophobic properties and the lower surface having hydrophilic properties, whereby fluid at the upper surface tends to wick towards the lower surface, wherein the crotch panel further includes a barrier layer underlying the absorbent layer, the barrier layer inhibiting fluid from passing through the crotch panel, and wherein the barrier layer bas first and second plies, the first ply being a fluid barrier material and the second ply being a fabric ply.

27. The undergarment of claim 26, the undergarment and crotch panel being comprised of washable materials whereby the undergarment is reusable.

28. The undergarment of claim 27 wherein the barrier layer defines an outer surface on the undergarment in the crotch area.

29. The undergarment of claim 27 wherein the crotch area of the undergarment has a fabric layer defined by the body portion, and the barrier layer overlies the crotch area fabric layer.

30. The undergarment of claim 27 wherein the crotch panel includes an additional fabric layer disposed between the absorbent layer and the barrier layer.

31. The undergarment of claim 30 wherein the additional fabric layer and the absorbent layer are quilted together.

32. The undergarment of claim 27 wherein the crotch panel includes a target marking which indicates the proper placement of the pad on the crotch panel.

33. The undergarment of claim 27 wherein the undergarment is a panty.

34. The undergarment of claim 28 wherein the barrier layer is immediately adjacent the absorbent fabric layer.

35. The undergarment of claim 27 wherein the fluid barrier material is laminated to the fabric ply.

36. The undergarment of claim 27 wherein the fabric ply defines an outer surface of the undergarment in the crotch area.

37. The undergarment of claim 27 wherein the undergarment is comprised of washable materials, whereby the undergarment is reusable.

38. The undergarment of claim 28 wherein the undergarment includes an additional fabric layer disposed between the absorbent fabric layer and the barrier layer.

39. The undergarment of claim 38 wherein the additional fabric layer and the fluid-retaining fabric layer are quilted together.

40. An undergarment for use with an absorbent pad, the undergarment comprising:

a body portion with an upper waist opening and two lower leg openings defining a crotch area therebetween, the body portion having a crotch panel associated with the crotch area, the crotch panel including a single-ply fluid absorbent fabric layer having upper and lower surfaces, the upper surface including yarns for being releasably held by said pad, the upper surface further having hydrophobic properties and the lower surface having hydrophilic properties, whereby fluid at the upper surface tends to wick towards the lower surface, wherein the crotch panel includes a target marking which indicates the proper placement of the pad on the crotch panel.

\* \* \* \* \*

UNITED STATES PATENT AND TRADEMARK OFFICE
CERTIFICATE OF CORRECTION

PATENT NO. : 5,778,457

DATED : July 14, 1998

INVENTOR(S) : David W. Conway

It is certified that error appears in the above-identified patent and that said Letters Patent is hereby corrected as shown below:

On the title page, after the Abstract, replace "40 claims" with --41 claims--;

Column 7, line 49 (claim 12), change "of claim 1" to read --of claim 11--;

Delete Claims 21-40, column 8, line 16 through column 10, line 21, and replace with the following correct claims 21-41:

--21. In combination:
 a quick-attach absorbent pad for use with an undergarment, the pad comprising an upper surface and a lower surface containing a fluid absorbent material therebetween and being sized to fit against a crotch panel of said undergarment with the lower surface of the pad adjacent said crotch panel, the pad further comprising a plurality of hook fasteners associated with the pad lower surface and adapted to releasably attach the pad to yarn loops of said crotch panel, and an undergarment having a crotch panel, the crotch panel including yarn loops for being releasably held by the hook fasteners of the pad, wherein the crotch panel includes an absorbent layer whereby fluid not retained by the pad may be absorbed by the absorbent layer, and wherein the crotch panel further includes a barrier layer underlying the absorbent layer, the barrier layer inhibiting fluid from passing through the crotch panel, wherein the barrier layer has first and second plies, the first ply being a fluid barrier material and the second ply being a fabric ply.

22. The combination of claim 21 wherein the crotch panel includes an additional fabric layer disposed between the absorbent layer and the barrier layer.

23. The combination of claim 22 wherein the additional fabric layer and the absorbent layer are quilted together.

UNITED STATES PATENT AND TRADEMARK OFFICE
CERTIFICATE OF CORRECTION

PATENT NO. : 5,778,457
DATED : July 14, 1998
INVENTOR(S) : David W. Conway

It is certified that error appears in the above-identified patent and that said Letters Patent is hereby corrected as shown below:

24. The combination of claim 21 wherein the crotch panel includes a target marking which indicates the proper placement of the pad on the crotch panel.

25. The combination of claim 21 wherein the undergarment is a panty.

26. In combination:
  a quick-attach absorbent pad for use with an undergarment, the pad comprising an upper surface and a lower surface containing a fluid absorbent material therebetween and being sized to fit against a crotch panel of said undergarment with the lower surface of the pad adjacent said crotch panel, the pad further comprising a plurality of hook fasteners associated with the pad lower surface and adapted to releasably attach the pad to yarn loops of said crotch panel, and an undergarment having a crotch panel, the crotch panel including yarn loops for being releasably held by the hook fasteners of the pad, wherein the crotch panel includes a target marking which indicates the proper placement of the pad on the crotch panel.

UNITED STATES PATENT AND TRADEMARK OFFICE
CERTIFICATE OF CORRECTION

PATENT NO. : 5,778,457
DATED : July 14, 1998
INVENTOR(S) : David W. Conway

It is certified that error appears in the above-identified patent and that said Letters Patent is hereby corrected as shown below:

27. An undergarment for use with an absorbent pad, the undergarment comprising: a body portion with an upper waist opening and two lower leg openings defining a crotch area therebetween, the body portion having a crotch panel associated with the crotch area, the crotch panel including a single-ply fluid absorbent fabric layer having upper and lower surfaces, the upper surface including yarns for being releasably held by said pad, the upper surface further having hydrophobic properties and the lower surface having hydrophilic properties, whereby fluid at the upper surface tends to wick towards the lower surface, wherein the crotch panel further includes a barrier layer underlying the absorbent layer, the barrier layer inhibiting fluid from passing through the crotch panel, and wherein the barrier layer has first and second plies, the first ply being a fluid barrier material and the second ply being a fabric ply.

28. The undergarment of claim 27, the undergarment and crotch panel being comprised of washable materials whereby the undergarment is reusable.

29. The undergarment of claim 27 wherein the barrier layer defines an outer surface on the undergarment in the crotch area.

30. The undergarment of claim 27 wherein the crotch area of the undergarment has a fabric layer defined by the body portion, and the barrier layer overlies the crotch area fabric layer.

31. The undergarment of claim 27 wherein the crotch panel includes an additional fabric layer disposed between the absorbent layer and the barrier layer.

32. The undergarment of claim 31 wherein the additional fabric layer and the absorbent layer are quilted together.

UNITED STATES PATENT AND TRADEMARK OFFICE
CERTIFICATE OF CORRECTION

PATENT NO. : 5,778,457
DATED : July 14, 1998
INVENTOR(S) : David W. Conway

It is certified that error appears in the above-identified patent and that said Letters Patent is hereby corrected as shown below:

33. The undergarment of claim 27 wherein the crotch panel includes a target marking which indicates the proper placement of the pad on the crotch panel.

34. The undergarment of claim 27 wherein the undergarment is a panty.

35. The undergarment of claim 27 wherein the barrier layer is immediately adjacent the absorbent fabric layer.

36. The undergarment of claim 27 wherein the fluid barrier material is laminated to the fabric ply.

37. The undergarment of claim 27 wherein the fabric ply defines an outer surface of the undergarment in the crotch area.

38. The undergarment of claim 27 wherein the undergarment is comprised of washable materials, whereby the undergarment is reusable.

39. The undergarment of claim 27 wherein the undergarment includes an additional fabric layer disposed between the absorbent fabric layer and the barrier layer.

40. The undergarment of claim 39 wherein the additional fabric layer and the absorbent fabric layer are quilted together.

UNITED STATES PATENT AND TRADEMARK OFFICE
CERTIFICATE OF CORRECTION

PATENT NO. : 5,778,457
DATED : July 14, 1998
INVENTOR(S) : David W. Conway

It is certified that error appears in the above-identified patent and that said Letters Patent is hereby corrected as shown below:

41. An undergarment for use with an absorbent pad, the undergarment comprising:

a body portion with an upper waist opening and two lower leg openings defining a crotch area therebetween, the body portion having a crotch panel associated with the crotch area, the crotch panel including a single-ply fluid absorbent fabric layer having upper and lower surfaces, the upper surface including yarns for being releasably held by said pad, the upper surface further having hydrophobic properties and the lower surface having hydrophilic properties, whereby fluid at the upper surface tends to wick towards the lower surface, wherein the crotch panel includes a target marking which indicates the proper placement of the pad on the crotch panel.--.

Signed and Sealed this

Thirtieth Day of March, 1999

Attest:

Q. TODD DICKINSON

Attesting Officer

Acting Commissioner of Patents and Trademarks